United States Patent [19]

Finkelstein

[11] Patent Number: 4,657,763

[45] Date of Patent: Apr. 14, 1987

[54] COMBINED CHRYSOTHERAPEUTIC AGENTS FOR AUTOIMMUNE DISEASES

[75] Inventor: Abraham E. Finkelstein, Buenos Aires, Argentina

[73] Assignee: Michael Ebert, Mamaroneck, N.Y.

[21] Appl. No.: 772,057

[22] Filed: Sep. 3, 1985

[51] Int. Cl.$^4$ .................... A61K 31/28; A61K 33/24
[52] U.S. Cl. .................................... 424/131; 514/495
[58] Field of Search ........................ 424/131; 514/495

[56] References Cited

PUBLICATIONS

Chem. Abst. 95 (1981) 194766j.
Chem. Abst. 99 (1983) 128198g.

Primary Examiner—Stanley J. Friedman
Attorney, Agent, or Firm—Michael Ebert

[57] ABSTRACT

Lysosomal enzymes and superoxide radicals ($O_2^-$) are potent mediators of rheumatoid inflammation. It is known that gold sodium thiosulphate (GTS), an injectable gold compound, inhibits lysosomal enzymes activity without however affecting its release, whereas auranofin (AF), an oral gold compound, inhibits such release but not enzyme activity. And while AF inhibits the generation of $O_2^-$, GTS is without significant effect. It has been discovered, using $O_2^-$ production as an indicator of respiratory burst, that subtherapeutic concentrations of the oral gold having only partial inhibitory activity on $O_2^-$ production, give rise to greatly enhanced inhibitory activity in such production when the oral gold is functionally combined with the otherwise inactive injectable gold. The effect of this combination of drugs is synergistic in that it far exceeds the sum of the individual inhibitory activities of the oral and injectable gold compounds. A further increase in $O_2^-$ production inhibition is realized by adding to the combination of gold compounds hydroxychoroquine, an antimalarial agent.

5 Claims, No Drawings

COMBINED CHRYSOTHERAPEUTIC AGENTS FOR AUTOIMMUNE DISEASES

BACKGROUND OF INVENTION

1. Field of Invention

This invention relates generally to drug therapy in the treatment of autoimmune diseases, and more particularly to the treatment of rheumatoid arthritis by the combined synergistic action of different gold compounds.

2. Status of Prior Art

Leucocytes, a type of white cell or corpuscle found in human blood is capable of ingesting disease-producing bacteria found in the body. These defenders against infection are known as phagocytes or eating cells, and the ingestive process as phagocytosis. Phagocytes are the body's first line of defense against invading microorganisms.

An antigen is any substance which when introduced into the body induces an immune response leading to acquired immunity. The immune response results in the formation of specific antibodies. These circulate in the bloodstream to develop humoral immunity or act to increase the number of reactive cells, called lymphocytes, to develop cell-mediated immunity, or both.

The concern of the present invention is with autoimmune diseases in which antibodies are produced against an individual's own tissues by reason of some malfunction of the immune system. The immune system, in addition to defending the body against infectious agents, also promotes homeostasis, that is the maintenance of normal conditions, as by removing damaged cellular elements and by supporting immunological self-tolerance. When the mechanism of self-tolerance breaks down, various disease states may subsequently occur such as rheumatoid arthritis (RA), hemolytic anemia and other autoimmune diseases.

In joints chronically affected by RA, the normally delicate synovial membrane develops many villous folds and thickens as a result of increased numbers of synovial lining cells and the colonization of lymphocytes and plasma cells. The colonizing cells which are initially perivenular, later form lymphoid follicles having germinal centers, synthesize rheumatoid factors and other immunoglobulins.

The use of water-soluble gold compounds, such as gold sodium thiomalate or thiosulphate, against active joint inflammation is well known. The usual procedure is to inject the patient at weekly intervals with a 10 mg. dose the first week, 25 mg. the second and 50 mg. thereafter at weekly intervals until a total of 1 Gm. has been delivered or a significant improvement becomes apparent. Hydroxychloroquine is known to occasionally control symptoms of mildly active RA.

Excessive production of superoxide radicals ($O_2^-$) and lysosomal enzymes by inflammation mediator cells like polymorphonuclear leukocytes, macrophages, and platelets gives rise to a sustaining chain of events leading to tissue injury. Defense mechanisms involve a highly complex cascade of reactions with the participation of endogenous inhibitors of inflammation like superoxide dismutases, antiproteases like alpha$_1$-antitrypsin, alpha$_2$-macroglobulin and antioxidants or free radical scavengers like ceruplasmin. (See: Weissman, G et al; Leucocytes as Secretory Organs of Inflammation., *Advances in Inflammation Research*, 1:95-112, 1979. Edited by G. Weissman et al., Raven Press, New York, 1979).

Oxidative damage by free radicals on circulating human gamma globulin (IgG) induces IgG aggregation with all the pathophysiological properties of immune-complexes present in the plasma and synovial fluid of patients with rheumatoid arthritis. (See: Jasin, H.; Generation of IgG Aggregates by the Myeloperoxidase-hydrogen-peroxide System, *The Journal of Immunology*, 130: 1918-1923, 1983).

The phagocytosis of such complexes may perpetuate the production and damaging effects of lysosomal enzymes and oxygen radicals. Superoxide radicals or free radicals are products of many biological reactions of living organisms with oxygen. The survival of aerobic organisms in an oxygen environment entails a complex interplay between the products of oxygen consumption by living cells and the ability of the organism to control $O_2$ metabolites. Oxygen consumption results in the formation of free radicals $O_2^-$ (Superoxide anion radical), $H_2O_2$ (hydrogen peroxide) and OH (hydroxyl radical). (See: Free Radicals in Medicine and Biology. *Acta Physiologica Scandinavica* Symposium Upsala, 1980).

Therapeutic interference with these mediators constitutes one of the properties found desirable in so called "disease modifying agents" or "slow acting antirheumatic drugs". Auranofin (AF) an oral chrysotherapeutic agent effective in the treatment of rheumatoid arthritis, is characterized, as are the injectable gold compounds, as a slow acting drug for the control of rheumatoid inflammatory response. (See: Finkelstein, A. E. et al.; Auranofin New Oral Gold Compound for Treatment of Rheumatoid Arthritis, *Ann. Rehum. Diseases*, 35: 251-257, 1976; Blodget, Jr., C. R., Hener, A. M., and Pietrusko, G. R., Auranofin: A Unique Oral Chrysotherapeutic Agent, *Seminar in Arthritis and Rheumatism*, 12:255-273, 1984).

While AF produces a significant dose-dependent inhibition of lysosomal enzyme release and super-oxide generation during immune-complex phagocytosis, we have found in previous studies that gold sodium thiosulphate (GTS), an injectable gold compound, is ineffective at therapeutic blood gold levels. (See: Finkelstein et al., Effect of Auranofin a New Antiarthritic Agent on Immune Complex Induced Release of Lysosomal Enzymes from Human Leucocytes, *Inflammation*, 2: 143-50, 1977; Finkelstein et al.; Auranofin and Lysosomal Enzymes, *J. Rheumatology* 9 (Suppl. 8), 46-53, 1982; Roisman, F., D. Walz and A. E. Finkelstein; Superoxide Radical Production by Human Leucocytes Exposed to Immune Complexes, *Inflammation*, 7: 355-362, 1983).

SUMMARY OF INVENTION

The main object of this invention is to provide for the treatment of an autoimmune disease a combination of chrysotherapeutic agents that is far more effective for this purpose than these agents when individually administered.

More particularly, an object of this invention is to provide an efficacious treatment for rheumatoid arthritis resulting in a substantially complete remission of this disease.

Briefly stated, these objects are attained by administering to a patient a combination of chrysotherapeutic agents which inhibit the production in the body of lysosomal and superoxide radicals ($O_2^-$), these being potent mediators of rheumatoid inflammation.

It is known that gold sodium thiosulphate (GTS), as an injectable gold compound, inhibits lysosomal activity without however affecting its release, whereas auranofin (AF), an oral gold compound, inhibits such release but not enzyme activity. And while AF inhibits the generation of $O_2^-$ production, GTS is without significant effect. It has been discovered, using $O_2^-$ production as an indicator of respiratory burst, that subtherapeutic concentrations of the oral gold having only partial inhibitory activity on $O_2^-$ production, give rise to greatly enhanced inhibitory activity in such production when the oral gold is functionally combined with the otherwise inactive injectable gold. The effect of this combination of drugs is synergistic in that it far exceeds the sum of individual inhibitory activities of the oral and injectable gold compounds. A further increase of $O_2^-$ production ihhibition is realized by the addition to the combination of gold compounds of hydroxychoroquine, an anti-malarial agent.

DETAILED DESCRIPTION OF INVENTION

When exploring the effect of oral gold, we concentrated on different parenteral gold compounds and hydroxychloroquine (Plaquenil), singly and in combined form on the early events in human polymorphonuclear netrophyl activation by receptor mediated stimuli and particulate stimuli.

By the use of these different stimuli for the activation of the oxygen burst [Poly-L-Histidine opsonized Streptococci; the secretagoge phorbol Myristate acetate (PMA); the chemoatractant N-formyl-methionyl-leucilphenylalanine (FMLPO]of PMNs, three models of experimental systems for the study of synergistic activity was used. Poly-L-Histidine and FMLP represented mild rheumatoid disease activity and PMA, the strongest stimuli for the oxygen burst, constituted a model for high disease activity.

With these systems as models of different degrees of leucocytes activation, subtherapeutic and therapeutic concentrations of antiarthritic drugs were investigated for synergism, using superoxide ($O_2^-$) production as an indicator of the respiratory burst. We have discovered that subtherapeutic concentrations of oral gold with partial inhibitory activity on $O_2^-$ production, gave rise to greatly enhanced inhibitory activity on the generation of $O_2^-$ when it was combined with the inactive injectable gold. The arithmetic addition or sum of their individual inhibitory activity was far smaller than the inhibition obtained when they were used synergistically in combined form. By definition, synergism is said to occur in drug treatment when the response to one drug is enhanced by another.

As we presently understand this synergistic activity, the oral gold compound AF, because of its solubility in the lipid layers of the cellular membrane, renders this membrane permeable to the injectable gold compounds which are water soluble. This effect on cell penetrance of one gold compound upon another antiarthritic agent, gold, hydroxychloroquine or any other potential therapeutic agent acts to heighten the response of the effector system. The end result observed in our case is the 100% inhibition of superoxide radical production and luminol-dependent chemiluminescence (LDCL) when a combined pretreatment of the leucocytes takes place.

Furthermore, the treatment of leucocytes with oral gold, injectable gold and hydroxychloroquine, acting in combination, makes it possible to attack the disease complex at different cellular points with subtoxic concentrations of each drug, thereby creating conditions conducive to a remission of disease activity. Since this combined treatment technique is effective in rheumatoid arthritis, other autoimmune diseases like lupus erythemathousus, dermatomyositis, etc. may likewise benefit from a rational synergistic immunomodulatory therapy. The same synergistic effect of combined gold therapy is also applicable in organ transplants such as with the heart and kidney, to prevent organ rejection.

Material and Methods

Hanks' balanced salt solution—HBSS ph 7.3 was used for the assays and cell preparations—Human gamma globulin Fraction II, Ferri-cytochrome C (Iype III), dimethylsulfoxide (DMSO)phorbol-myristate acetate (PMA), N-formyl-methionyl-leucilphenylalanine (FMLP), histone Type II A and luminol-5 amino-2-3-dehidro-1-4 phtolozimdione were purchased from Sigma Chemical Co., St. Louis, Mo. Poly-L-Histidine (PHSTD), M.W. 10.300 from Miles Yeda, Rehovot, Israel, and Cytochalasin B from Makor Chemicals, Israel.

Streptococci group A were grown overnight in Brain Heart infusion broth, centrifuged and washed 3 times in saline, and resuspended in saline to a final O. D. of 10.000 Lettt units/ml Streptococci/Histone Type II A were prepared by dissolving histone in saline, (ph 6.5) to a concentration of 10 mg/ml. 10 ul of histone plus 10 ul of streptococci constituted the particulate stimuli for the luminol dependent chemiluminescence assays (LDCL).

Gold Compounds

Oral gold, Auranofin (AF)-2,3,4,6, tetra-O-acetyl-1-thio-b-D-glucopyranosato (triethylphosphine) gold with 0.29% content of Au was obtained from Smith, Kline and French Lab., Philadelphia. "Crition", Gold sodium thiosulphate (GTS) with a 37% content of Au; Solganol, Gold Sodium thioglucose (GTG) with 50% of Au; and Miocrin, Gold Sodium thiomalate (GTM) with 48% Au, were commercially obtained. AF was dissolved in DMSO to a mother solution of 1 mg/ml., GTM in d.water, 0.5 mg/ml., GTG in DMSO, 5 mg/ml. and GTS in d.w. Hydroxychloroquine (Plaquenil) was obtained from Sterling-Winthrop Research Institute, Rensselaer, N.Y.

Leucocytes

Blood from normal controls and blood from synovial fluid from patients with active rheumatoid arthritis were collected simultaneously into plastic tubes containing heparin (10 units/ml.) for the isolation of PMNs. The synovial fluid was diluted 1:1 in PBS and centrifuged al 200 g 15-20 min. The pellet of leucocytes were washed three times with HBSS.

The leucocytes from the heparinized blood were isolated by dextran sedimentation and hypotonic lysis of erthrocytes was done with 0.85% ammonium chloride for 5 min. at room temperature. The leucocytes were resuspended in HBSS buffered with 3 mM HEPES ph 7.3, and containing 5% heat inactivated fetal calf serum. The leucocyte suspensions were placed on crushed ice and were found to retain their LDCL and $O_2^-$ generation properties for approximately 4–5 hours.

Superoxide Generation

Leucocytes ($2 \times 10^6$) suspended in HBSS were treated for 5 min. at 37° C. with different concentrations of AF alone, injectable gold compounds alone and with their combination. Superoxide generation was then induced either by the addition of Poly-L-Histidine (PHSTD) $10^{-5}$M, dissolved in saline at ph 6.5, 10 mg/ml. adding 100 ug for PMNs stimulation; PMA ($10^{-6}$M) 50 ug and FMLP ($10^{-7}$M) 0.05 ug/ml. added to the reaction mixtures and both dissolved in DMSO, the last one (FMLP) added together with Cytochalasin B (2.5 ug) also dissolved in DMSO for PMN activation in the presence of 100 um of Cytochrome C.

Superoxide Dismutase (SOD)—20 ug/ml. was included as a control for the identification of superoxide radicals ($O_2^-$). After 10 min. of incubation at 37° C. the tubes were centrifuged at 2000 g for 3 min. and the absorbance at 550 nm of the supernatant fluids was determined in a Unicam Sl 1700 ultraviolet double beam spectrophotometer. The amount of $O_2^-$ formed was calculated from the formula $=2.1 \times 10^{-4}$M. $cm^{-1}$ and expressed as nanomoles per given number of leucocytes. (See: Ginsburg, I., Borinski, R, and Rainsford, K.; Poly-L-Histidine, a Potent Stimulation of Superoxide Generation by Human Blood Leucocytes: Mo dulation by Metabolic Inhibitors and Anti-inflammatory Drugs, *Inflammation*, In Press, 1985).

Luminol Dependent Chemiluminescence (LDCL)

To $13 \times 10$ mm. polyethylene tubes containing 0.9 ml. of HBSS $2 \times 10^6$ leucocytes preincubated at 37° C. during 5 min. with oral and injectable gold compounds was added. PMA (50mg.) or 50 ul of washed group A streptococci (Type 4) of an optical density of 2.0 at 540 nm, and 10 ul of nuclear histone (100 ug) were added to the reaction mixture. After an additional incubation of 5 min. at 37° C. to allow the generation of radicals, 10 ul of luminol (2 mg/ml.) dissolved in DMSO was added. The tubes were vortexed and placed in a LKB Wallac 1250 luminometer for LDCL measurement. Readings were monitored after 20 sec. and each experiment was done by triplicates with the inclusion of controls after every third reading. (See: Ginsbury, I. and Borinski, R.; "Cocktails" of Soluble Ligands and Bacteria "opsonized" with Cationic and Anionic Ligands Trigger Intense Chemiluminescence and Superoxide Production by Leucocytes; In: *Cellular Chemiluminescence*, Edited by K. Van Dyke, CRC Press, 1984).

Test Results and Analysis

It is of background interest that the latest reports of clinical studies comparing the effectiveness of oral gold with the injectable gold indicated no difference. Either one, induces approximately from 40 to 50% of clinical improvement. (See: Horton, R.J.; Comparative Safety and Efficacy of Auranofin and Parenteral Gold Compounds; A Review, *Scand.Journal of Rheumatology*, Sup. 51, 100-110, 1983).

Data of the work performed with the above outlined procedures were subjected to statistical analysis, which points out the therapeutic synergistic potential of the combined gold action. Table 1 annexed hereto shows that 0.6 and 0.9 ug/ml of Auranofin (AF) inhibits 34 and 58% of $O_2$ generation respectively. Only when the leucocytes were pretreated with the combination of oral (AF) and injectable gold (GTS) did a 84 and 97% inhibition of $O_2^-$ production take place.

Table 2 annexed hereto shows that the inhibition of luminol dependent chemiluminescence (LDCL) is enhanced by the combination of both gold forms, these being gold thiosulphate (GTS), the injectable preparation which best inhibits LDCL when combined with oral gold. GTS alone at this concentration of 1 ug Au/ml. has no effect. Here, also, it is observed that with the "therapeutic blood gold levels" of 0.6 and 0.9 ug Au/ml. only when in combined form the gold pretreatment of the leucocytes, has its maximum effect: 72 and 92% inhibitions of LDCL.

We have found that the synergism resulting from the combined use of oral and injectable gold compound in inhibiting the generation of superoxide radicals is further enhanced by the addition to the combination of hydroxychloroquine, an anti-malarial agent, thereby opening up a new approach for the control of rheumatoid arthritis. Thus the synergistic activity of the different gold compounds, plus the anti-malarial agent operating concurrently in the body, function as rheumatoid arthritis disease remission-inducing agents. This makes possible a significant improvement in the treatment of rheumatoid arthritis and other autoimmune diseases.

Study with Rheumatoid Arthritis PMNs

When PMNs derived from patients with rheumatoid arthritis (RA) were compared with PMNs from healthy controls, it was found that RA PMNs's were different than normals, in the sense that they were "activated"; that is that they were releasing even before PMA stimulation, greater quantities of superoxide radicals. This activated stage of the RA leucocytes was only partially blocked by clinical concentrations of oral gold. Only when both golds were used injectable and oral, a complete normalization took place of the rheumatoid arthritis derived leucocytes from the peripheral blood or from the synovial fluid.

During the last decade, since the first publication of clinical and laboratory effectiveness of an oral gold compound in RA, great interest has been aroused on the need to explore the mechanism of gold action at a cellular and molecular level. Today there is little doubt that the old empirical concept of 1 Gm. course of injectable gold treatment of RA should be reevaluated in the light of the current great volume of experimental data which emanates from the comparative studies at a laboratory and clinical level of oral and injectable chrysotherapy.

During this research period it was learned that oral gold has physical, chemical, pharmacological and pharmacokinetic different properties than the available injectable gold compounds. Therefore, their combination in accordance with this invention brings into being a new pharmacuetical reality for the benefit of the sufferers of this crippling disease.

In practice, at least two of the three drug components in a treatment in accordance with the invention may be merged to form a composite drug to simplify the procedure.

TABLE 1

SYNERGISTIC EFFECT OF AURANOFIN AND GOLD SODIUM THIOSULPHATE EXPRESSED BY DIFFERENT ACTIVATORS OF $O_2^-$ PRODUCTION BY HUMAN LEUCOCYTES

| Gold compound | ug Au/ml | % Inhibition of $O_2^-$ generation by | | |
|---|---|---|---|---|
| | | PHSTD | FMLP | PMA |
| Auranofin (AF) | 0.03 | 0 | 0 | 0 |
| | 0.07 | 20 | 25 | 0 |
| | 0.15 | 48 | 65 | 6 |
| | 0.3 | 86 | 70 | 19 |
| | 0.6 | 90 | 78 | 34* |
| | 0.9 | 98 | 86 | 58* |
| | 1.4 | 97 | 88 | 70 |
| GTS | 3.7 | 0 | 0 | 0 |
| AF-GTS | 0.03 + 3.7 | 0 | 0 | 0 |
| | 0.07 + 3.7 | 52 | 85 | 0 |
| | 0.15 + 3.7 | 86 | 100 | 14 |
| | 0.3 + 3.7 | 97 | 100 | 49 |
| | 0.6 + 3.7 | 95 | 100 | 84* |
| | 0.9 + 3.7 | 98 | 100 | 97* |

TABLE 1-continued
SYNERGISTIC EFFECT OF AURANOFIN AND GOLD SODIUM THIOSULPHATE EXPRESSED BY DIFFERENT ACTIVATORS OF $O_2^-$ PRODUCTION BY HUMAN LEUCOCYTES

| Gold compound | ug Au/ml | % Inhibition of $O_2^-$ generation by | | |
|---|---|---|---|---|
| | | PHSTD | FMLP | PMA |
| | 1.4 + 3.7 | 98 | 100 | 100 |
| SOD | 20 | 98 | 98 | 98 |

*p < 0.005

Leucocytes (2 × 10⁶) were preincubated for 5 min at 37° C. with the drugs and then stimulated by PHSTD, FMLP and PMA in the presence of cytochrome C. PHSTD, FMLP and PMA induced the generation of nmoles of $O_2$ per 2 × 10⁶/10 min. being PMA the strongest stimuli of $O_2^-$ generation. Results are expressed as percent inhibition of $O_2$ generation and represent the average of 4 experiments performed with 4 different sources of leucocytes. Superoxide Dismutase (SOD)

TABLE 2
INHIBITION OF LDCL* INDUCED BY THE PMA ACTIVATED OXIGEN BURST OF HUMAN LEUCOCYTES

| AURANOFIN | ug Au/ml | 0.3 | 0.6 | 0.9 | 1.4 |
|---|---|---|---|---|---|
| | | % Inhibition of LDCL | | | |
| AF | | 20.5 | 47 | 67.5 | 81.5 |
| AF + GTS | (1 ug Au/ml) | 33 | 72 | 92 | 92 |
| AF + GTM | (1 ug Au/ml) | 20 | 50 | 70 | 86 |
| AF + GTG | (1 ug Au/ml) | 14 | 62 | 59 | 83 |

PMN (2 × 10⁶) were pretreated with increased concentrations of Auranofin alone or in combination with 1 ug Au/ml of different injectable gold compounds (GTS, GTM, GTG). Results are expressed as percent inhibition of 3 experiments with 3 different sources of leucocytes.
*Luminol Dependent Chemiluminescence.

I claim:
1. A method for treating an autoimmune disease comprising the step of administering to a patient suffering from the disease the combination of a first gold compound which is soluble in the lipid layers of the cellular membrane and a second gold compound which is water soluble, said two compounds being adminstered in respective amounts at which the two compounds function concurrently and act synergistically, said first compound being auranofin and the second compound being selected from a group consisting of gold sodium thiosulphate, gold sodium thiomalate and gold sodium thioglucose, the combination having dosage sufficient to effect a substantial remission of the disease.

2. A method as set forth in claim 1 wherein said disease is rhematoid arthritis.

3. A method as set forth in claim 1 further including the addition to the combination of hydroxychoroquine.

4. A composite drug for the treatment of an autoimmune disease constituted by auranofin gold compound combined with a water-soluble gold compound selected from a group consisting of gold sodium thiosulphate, gold sodium thiomalate and gold sodium thioglucose in respective amounts at which the two gold compounds function concurrently and act synergistically.

5. A composite drug as set forth in claim 1 further including hydroxychoroquine.

* * * * *